United States Patent [19]

Unsöld et al.

[11] 4,365,157

[45] Dec. 21, 1982

[54] FLUID ANALYZER UTILIZING A LASER BEAM

[75] Inventors: Eberhard Unsöld, Oberschleissheim; Gerhard Renner, Eichennau; Reiner Wechsung, Cologne, all of Fed. Rep. of Germany

[73] Assignee: Gesellschaft für Strahlen-und Umweltforschung mbH, Munich, Fed. Rep. of Germany

[21] Appl. No.: 271,376

[22] Filed: Jun. 8, 1981

Related U.S. Application Data

[63] Continuation of Ser. No. 82,603, Oct. 9, 1979, abandoned.

[30] Foreign Application Priority Data

Oct. 9, 1978 [DE] Fed. Rep. of Germany ....... 2844002

[51] Int. Cl.³ .............................................. B01D 59/44

[52] U.S. Cl. .................................. 250/282; 250/287; 250/423 P

[58] Field of Search .............. 250/281, 282, 283, 287, 250/288, 423 P, 432; 423/2

[56] References Cited

U.S. PATENT DOCUMENTS

| | | | |
|---|---|---|---|
| 3,626,181 | 12/1971 | Wernland | 250/281 |
| 3,914,655 | 10/1975 | Dreyfus et al. | 250/423 P |
| 4,025,790 | 5/1977 | Jetter et al. | 250/288 |
| 4,140,905 | 2/1979 | Polanyi | 250/423 P |
| 4,204,117 | 5/1980 | Aberle et al. | 250/287 |
| 4,296,322 | 10/1981 | Wechsung | 250/287 |

*Primary Examiner*—Bruce C. Anderson
*Attorney, Agent, or Firm*—Spencer & Kaye

[57] ABSTRACT

A method for studying a fluid by forming a stream of the fluid, exciting the stream by causing a laser beam to impinge thereon to produce secondary particles or quanta, and subjecting the resulting secondary particles or quanta to an analysis operation in an analyzer.

8 Claims, 3 Drawing Figures

FLUID ANALYZER UTILIZING A LASER BEAM

CROSS-REFERENCE TO RELATED APPLICATION

This application is a continuation of application Ser. No. 82,603, filed Oct. 9, 1979 now abandoned.

BACKGROUND OF THE INVENTION

The present invention relates to the analysis of fluids, including liquids or mixtures thereof.

There are a number of known methods for analyzing gases or liquids. However, all these methods have limited sensitivity. The expenditures required to increase sensitivity increase considerably, with the increase in sensitivity, as is true for many measuring methods.

One way to analyze gases is to ionize the gases in an electron surge ion source and to then perform the analysis proper with the aid of a mass spectrometer, e.g. a quadrupole mass spectrometer. In such a method gases to be examined unavoidably come into contact with the structural elements of the ion source, where they are precipitated. This is a drawback not only because it causes corrosion of the structural components, but particularly also because it gives rise to effects due to prior contaminations which falsify later measurements.

SUMMARY OF THE INVENTION

It is an object of the present invention to eliminate such drawbacks from a method of the above-mentioned type.

This and other objects are achieved, according to the present invention by exciting a stream of fluid to be analyzed by means of a laser beam and utilizing, in a known manner, the resulting secondary particles or quanta for the analysis proper. The fluid stream can travel freely in space in the region where the laser beam impinges thereon so that no other components need be located there which could produce "memory" effects.

The laser beam is capable of producing a strong excitation of the fluid stream so that, for example, the ionization probability is very high. Due to the free flow of the fluid stream, there is no problem in arranging the entrance opening of an analysis device in optimum proximity to the point of intersection of the laser beam with the fluid stream. This enables the present invention to attain an extremely high sensitivity.

It is particularly advisable to subject the ions created during bombardment of the fluid stream to a mass analysis employing a time of flight mass spectrometer, known per se. This measure has the result that the analysis result will be available very quickly.

Further advantages, offered by the present invention, are: that the fluid stream can be injected with the aid of a nozzle into a vacuum chamber in such quantities that no significant deterioration of the vacuum in the chamber occurs; that the laser light which is directed approximately perpendicularly to the exit direction of the fluid can be focused on a point disposed immediately downstream of the exit opening of the nozzle; and that the entrance opening of the analyzer can be arranged at an optimum distance from the point of intersection of the laser beam with the fluid stream. A pulsed laser beam as well as a fluid stream pulsed in approximately the same rhythm can be used for this purpose. This contributes to minimizing the quantity of fluid flowing into the vacuum chamber.

DESCRIPTION OF THE PREFERRED EMBODIMENTS

Figure 1:
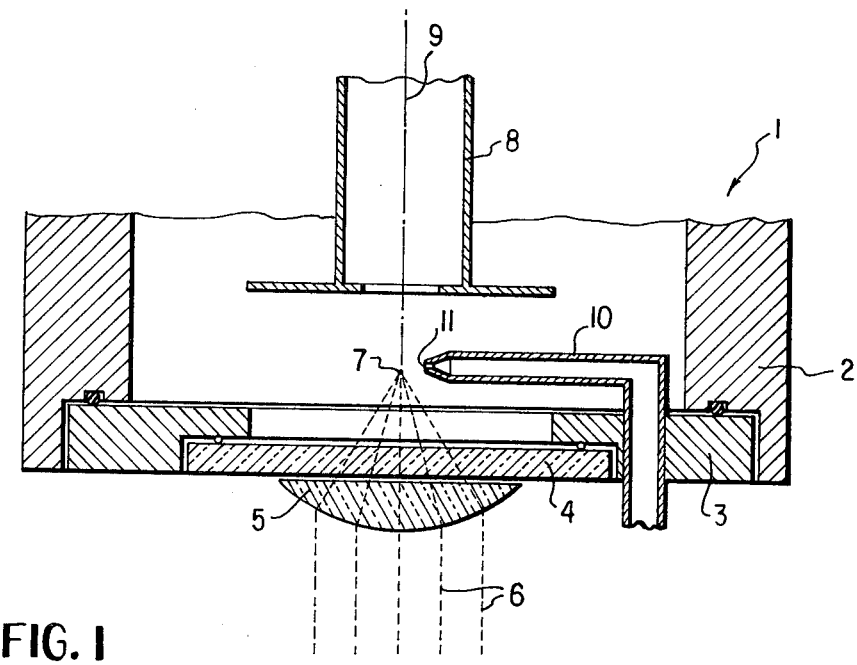
FIGS. 1, 2, and 3 are cross-sectional, detail views of three preferred embodiments of an apparatus for practicing the invention.
Figure 2:
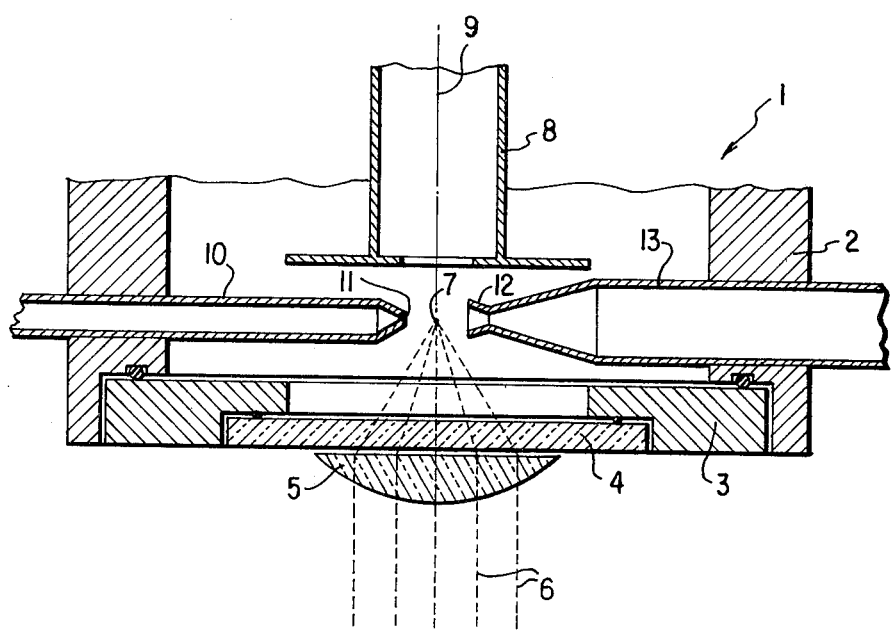

FIGS. 1 and 2 both show part of a vacuum chamber 1 which includes an essentially tubular section 2 and a cover flange 3 for closing the frontal face opening of section 2. The cover flange 3 is provided with a cover glass 4 which is transparent to laser light and is set into flange 3 in a vacuum tight manner. On the outside of this cover glass 4 there rests a lens system 5 which acts to focus, or concentrate, a collimated laser beam 6 at a point 7 in the interior of the vacuum chamber. The device for generating the laser beam is not shown and can be constituted by any suitable known laser light source. The time of flight tube 8 of a known time of flight mass spectrometer is disposed within the vacuum chamber 1 in such a manner that the laser beam 6 and the illustrated section of the time of flight tube 8 have a common axis 9. Advisably, an ion optical system may be placed upstream of the time of flight tube 8; however, to better depict the contribution of the invention, this is not shown here.

In the embodiment of FIG. 1, an inlet tube 10 extends through the cover flange 3 and has a nozzle opening 11 in the vicinity of the focal point, or point of convergence, 7 of the laser beam. The fluid to be examined is introduced into the vacuum chamber 1 through this inlet tube in such a manner that the focal point 7 of the laser beam falls within the fluid stream. The desired ions are generated by bombarding the fluid stream with a pulsed laser beam and are then analyzed with the aid of the time of flight mass spectrometer of which tube 8 forms a part.

In the embodiment of FIG. 1, the mass rate at which fluid to be examined can be introduced must be limited to a value which will not substantially impair the vacuum.

In the embodiment of FIG. 2, the opening 12 of a suction pipe 13 is disposed in line with the nozzle end 11 of the inlet tube 10, which has here been brought through a side wall of section 2. The fluid carrying members are arranged so that the focal point 7 of the laser beam lies between the nozzle 11 and the opening 12. In this embodiment, a relatively strong fluid stream can be provided without impairing the vacuum since the fluid stream is removed directly from the vacuum chamber 1 through tube 13. Tubes 10 and 13 are arranged in such a manner that the fluid stream to be examined travels approximately perpendicularly to the axis 9 of the analyzing system.

Figure 3:
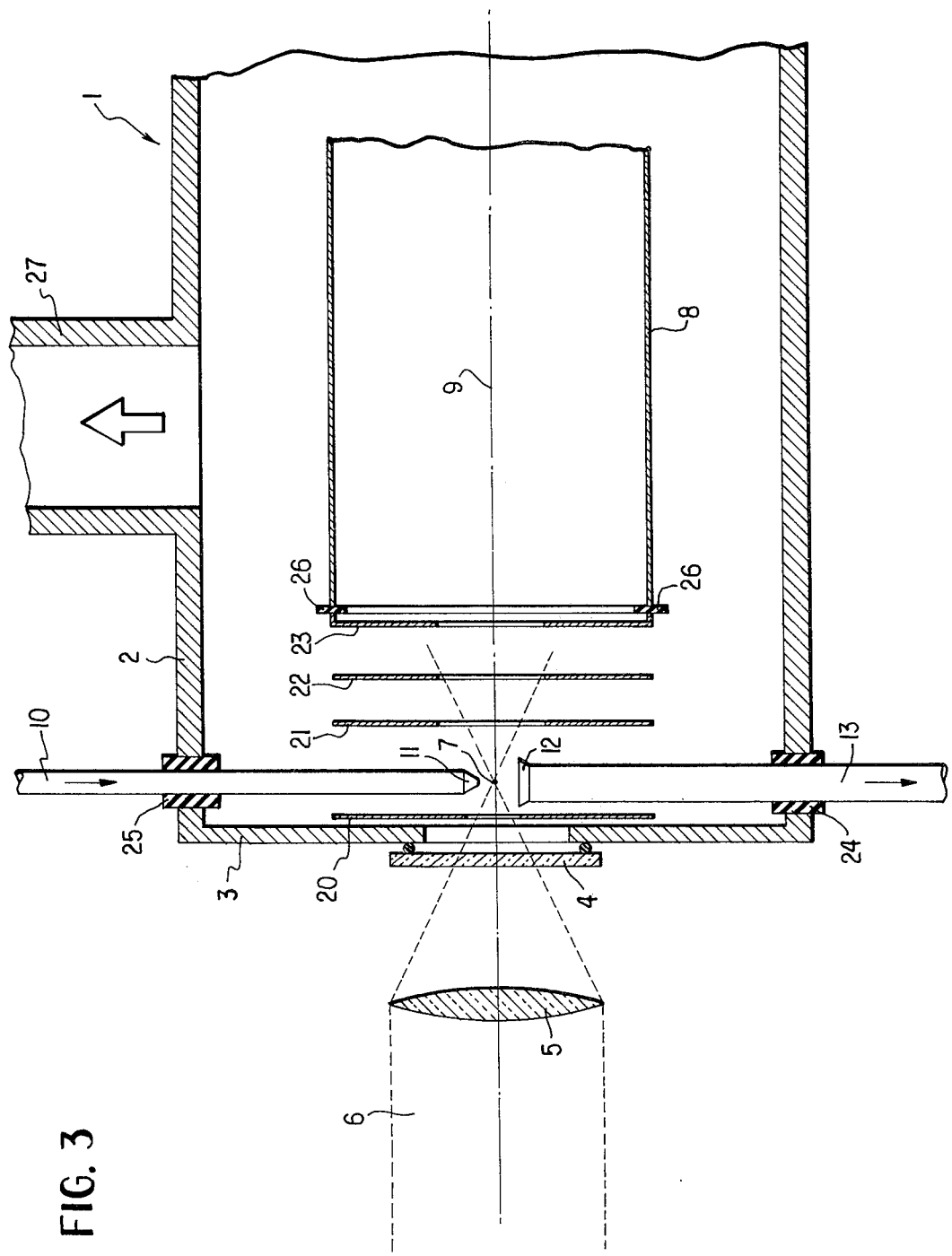

FIG. 3 shows the arrangement of an ion optical system between the focal point 7 of the laser beam and the entrance of the time of flight tube 8. This ion optical system consists of a pulse electrode 20 and three electrodes 21, 22 and 23 forming an immersion particle lens. The mountings and connections for the power supply as well as the power supply itself have been omitted for purposes of clarity. The electric field between electrodes 20 and 21 accelerates the particles towards the mass spectrometer 8, which can be constituted by a device sold under the designation Lamma 500 by Leybold-Heraeus GmbH, Cologne, Federal Republic of Germany. The electrodes 20, 21, 22 and 23 serve for collimation of the particles produced at the laser focus 7. All potentials of the elements 10, 13, 20, 21, 22. 23 and 8 can be chosen for a proper performance of the instrument. The inserts 24, 25 and 26 serve as insulators. To evacuate the vacuum chamber 1, a flange 27 connectable to a commercial vacuum pump is provided.

It will be understood that the above description of the present invention is susceptible to various modifications, changes and adaptations, and the same are intended to be comprehended within the meaning and range of equivalents of the appended claims.

What is claimed is:

1. A method for studying a fluid comprising: forming a stream of such fluid in a vacuum chamber; exciting the stream by causing a pulsed laser beam to impinge thereon to produce photoionized ions of molecules of the fluid; and subjecting the resulting photoionized ions to a mass analysis operation in a time of flight mass spectrometer including a time of flight tube constituting the input portion of the spectrometer and enclosing an electric field free region, the tube being disposed in the vacuum chamber, said step of subjecting being carried out by causing the ions to pass through the field free region of the tube.

2. Method as defined in claim 1 wherein said step of forming a fluid stream is carried out by injecting the fluid into the vacuum chamber via a nozzle at a rate selected to prevent significant deterioration of the vacuum level in the chamber, said step of exciting is carried out by directing the laser beam approximately perpendicularly to the direction of injection of the fluid into the chamber and concentrating the beam to a point in the fluid stream directly in front of the exit opening of the nozzle, and said step of subjecting is carried out by disposing the entrance opening of the analyzer at an optimum distance from the point of intersection of the laser beam with the fluid stream.

3. Method as defined in claim 2 wherein said step of forming a stream comprises pulsing the fluid stream in approximately the same rhythm as the pulsed laser radiation.

4. Apparatus for studying a fluid comprising: a vacuum chamber; means for generating a pulsed laser beam and converging the beam to a point within said chamber; means for directing an unconfined stream of the fluid along a path traversing the beam convergence point; and means for analyzing the photoionized ions of molecules of the fluid produced by impingement of the beam on the fluid, said analyzing means including a time of flight mass spectrometer provided with a time of flight tube constituting the input portion of the spectrometer and enclosing an electric field free region, said tube being located in proximity to the beam convergence point for permitting the ions to enter said tube and pass through said field free region.

5. Apparatus as defined in claim 4 wherein said vacuum chamber includes a wall portion transparent to laser radiation, said beam generating and converging means are disposed outside of said vacuum chamber in such a manner that the laser beam enters said vacuum chamber through said wall portion, and said stream directing means include a conduit extending into said vacuum chamber and an exit nozzle disposed at the outlet end of said conduit and located upstream of the beam convergence point, said nozzle being oriented to cause the fluid stream to exit therefrom approximately perpendicularly to the laser beam axis.

6. Apparatus as defined in claim 5 wherein said mass spectrometer has its input portion oriented to define an input path coaxial with the laser beam and so positioned that the point of intersection of the laser beam with the fluid stream lies between said beam generating and converging means and said input portion.

7. Apparatus as defined in claim 6 wherein said input portion comprises an ion optical system.

8. Apparatus as defined in claim 5, 6 or 7 wherein said stream directing means further comprise a suction line having an inlet opening aligned with the outlet end of said exit nozzle for withdrawing the fluid stream from said chamber after the stream has exited from said nozzle and passed beyond the beam convergence point.

* * * * *

UNITED STATES PATENT AND TRADEMARK OFFICE
CERTIFICATE OF CORRECTION

PATENT NO. : 4,365,157

DATED : December 21, 1982

INVENTOR(S) : Eberhard Unsöld et al.

It is certified that error appears in the above-identified patent and that said Letters Patent is hereby corrected as shown below:

On the title page, Item (54) should read:

-- Fluid Analysis Utilizing A Laser Beam --.

Assignee under Item (73) should read:

-- Gesellschaft für Strahlen- und Umweltforschung mbH, München, Neuherberg, Fed. Republic of Germany --

Signed and Sealed this

Seventh Day of June 1983

[SEAL]

Attest:

DONALD J. QUIGG

Attesting Officer

Acting Commissioner of Patents and Trademarks